United States Patent
Reyes et al.

(10) Patent No.: US 10,321,976 B2
(45) Date of Patent: Jun. 18, 2019

(54) COMPOSITE EXTRACTION PEN

(71) Applicants: Hari Mark Reyes, Portland, OR (US); John Marshall Arthur Turner, Beaverton, OR (US)

(72) Inventors: Hari Mark Reyes, Portland, OR (US); John Marshall Arthur Turner, Beaverton, OR (US)

(*) Notice: Subject to any disclaimer, the term of this patent is extended or adjusted under 35 U.S.C. 154(b) by 0 days.

(21) Appl. No.: 15/390,335

(22) Filed: Dec. 23, 2016

(65) Prior Publication Data
US 2017/0348070 A1    Dec. 7, 2017

Related U.S. Application Data

(60) Provisional application No. 62/344,810, filed on Jun. 2, 2016.

(51) Int. Cl.
| | |
|---|---|
| *A61C 3/00* | (2006.01) |
| *A61C 5/62* | (2017.01) |
| *A61C 5/66* | (2017.01) |
| *A61C 1/08* | (2006.01) |
| *A61C 1/00* | (2006.01) |

(52) U.S. Cl.
CPC .............. *A61C 5/62* (2017.02); *A61C 1/0015* (2013.01); *A61C 1/088* (2013.01); *A61C 5/66* (2017.02); *A61C 2202/01* (2013.01); *A61C 2204/002* (2013.01)

(58) Field of Classification Search
CPC ........... A61C 5/62; A61C 5/66; A61C 1/0015; A61C 1/088; A61C 2204/002
See application file for complete search history.

(56) References Cited

U.S. PATENT DOCUMENTS

| 4,330,280 A | * | 5/1982 | Dougherty | A61C 9/0026 222/326 |
| 4,582,488 A | * | 4/1986 | Newman | A61C 5/55 433/81 |
| 4,704,088 A | * | 11/1987 | Newman | A61C 5/55 433/81 |
| 4,933,291 A | * | 6/1990 | Daiss | B01L 3/0275 356/244 |
| 5,690,618 A | * | 11/1997 | Smith | A61M 5/20 128/DIG. 1 |
| 5,692,642 A | * | 12/1997 | Brattesani | B05C 17/01 221/199 |
| 6,159,161 A | * | 12/2000 | Hodosh | A61M 5/20 600/561 |
| 6,312,254 B1 | * | 11/2001 | Friedman | A61C 5/62 433/32 |

(Continued)

*Primary Examiner* — Nicholas D Lucchesi
(74) *Attorney, Agent, or Firm* — Mark S Hubert (57) ABSTRACT

A lightweight, small footprint, composite extraction pen, for the delivery of dental filling composite from commercially available composite filled carpules. An electric linear actuator is housed in a slender, pen-like housing configured to accept, constrain and allow the rotational positioning of commercially available composite filled carpules. The carpules are contained within an adaptor that connects to the body of the pen. The linear actuator extends and retracts a piston through a bore in the carpule so as to exert pressure on the composite contained therein. The pen provides precise composite delivery while maintaining a highly visible dental environment.

7 Claims, 12 Drawing Sheets

(56) References Cited

U.S. PATENT DOCUMENTS

| | | | |
|---|---|---|---|
| 6,981,868 B2* | 1/2006 | Okawa | B05C 17/00593 |
| | | | 222/326 |
| 2007/0186923 A1* | 8/2007 | Poutiatine | A61J 7/0038 |
| | | | 128/200.14 |
| 2008/0144426 A1* | 6/2008 | Janssen | B01F 7/00216 |
| | | | 366/130 |
| 2012/0329006 A1* | 12/2012 | Pierson | A61C 9/0026 |
| | | | 433/90 |
| 2013/0090594 A1* | 4/2013 | Palmer | A61J 7/0053 |
| | | | 604/60 |
| 2014/0036616 A1* | 2/2014 | Ghosh | B01F 13/0027 |
| | | | 366/129 |

* cited by examiner

COMPOSITE EXTRACTION PEN

COPYRIGHT STATEMENT

A portion of the disclosure of this patent document contains material that is subject to copyright protection. The copyright owner has no objection to the facsimile reproduction by anyone of the patent document or the patent disclosure as it appears in the Patent and Trademark Office patent file or records, but otherwise reserves all copyright rights whatsoever.

FIELD

The present disclosure relates, in general, to dental devices, and more particularly to composite cavity filling technology.

BACKGROUND

In dentistry, once a decayed tooth has been drilled, it must be filled with a composite material. This historically comes is pre-filled carpules. These are bent, hollow polymer containers open on each end that that house the composite material. On the proximal end there is a cup frictionally sealed about its perimeter to the walls of the circular cross sectional carpule, and on the distal end there is a removable cap. Between the cap and the cup resides the composite. It is applied into the cavity by a pressure that is exerted on the cup such that the cup axially slides along the inside of the carpule and forces the composite out the distal end. The current applicators are large cumberson hand actuated pistons or air actuated cylinders. Besides each being large enough to obscure the dentist's view, each has its own drawbacks.

The precision of the hand actuated pistons are limited by the stability of the dentist's hands. This is difficult because of the force needed to drive the cylinder causes the dentist's hand to shake, and because of its physical size, the dentist cannot brace and fulcrum his hand against the patient's jaw/chin. The air actuated pistons need a source of compressed air to operate. This adds another cumbersome hose to complicate matters. The size of the current devices prevent a full view of the oral cavity, and their lack of stability results in many a "blind" filling.

The carpules have to commonly be replaced or swapped out when blending colors and materials. The dental assistant generally does this process, necessitating the transfer of the device and its hoses (in the case of the air actuated cylinder) around the patient. To complicate matters, the application of the composite is a time sensitive maneuver.

Thus, a smaller, more controllable, cordless device for the application of dental composite from conventional, commercially available carpules, would be a welcome improvement in the dental industry. It would allow a much better delivery of the dental filling composite. Such a solution is provided by the embodiments set forth below.

BRIEF SUMMARY

In accordance with various embodiments, a portable apparatus for the application of dental composite into a tooth to be filled is provided.

In one aspect, a composite extraction pen, configured to accept and allow the rotational positioning of commercially available composite filled carpules is provided. It is cordless and powered by a rechargeable battery, preferably inductively charged.

In another aspect, a linear actuator composite extraction device having a small footprint, a pen shaped housing and various engageable composite feed speeds is provided.

In yet a further aspect, an electronic linear actuator composite extraction device having ample power to extract the stiffest of dental filling composites and with an electronically adjustable delivery speed to address differing flowability composites.

In yet another aspect, a low profile composite extraction pen is provided capable of precise composite delivery while maintaining a highly visible environment for the dentist.

In yet another aspect, a lightweight composite extraction pen is provided that is capable of a stable composite delivery, directionally and delivery controlled with a minimal of lateral movement, adapted to accept different manufacture's carpules.

Various modifications and additions can be made to the embodiments discussed without departing from the scope of the invention. For example, while the embodiments described above refer to particular features, the scope of this invention also includes embodiments having different combination of features and embodiments that do not include all of the above described features.

BRIEF DESCRIPTION OF THE DRAWINGS

A further understanding of the nature and advantages of particular embodiments may be realized by reference to the remaining portions of the specification and the drawings, in which like reference numerals are used to refer to similar components.

DETAILED DESCRIPTION

While various aspects and features of certain embodiments have been summarized above, the following detailed description illustrates a few exemplary embodiments in further detail to enable one skilled in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. While various features are ascribed to different embodiments, it should be appreciated that the features described with respect to one embodiment may be incorporated with other embodiments as well. By the same token, however, no single feature or features of any described embodiment should be considered essential to every embodiment of the invention, as other embodiments of the invention may omit such features.

Unless otherwise indicated, all numbers herein used to express quantities, dimensions, and so forth, should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

The term "carpule" as used herein, refers to a sealed container filled with a flowable material that may be extracted from one end or an opening in the container by the application of force to or within the container.

The present invention relates to a novel design for an improved dental filling composite delivery device. Its predominant features are that it has a very small footprint, is cordless, lightweight, offers accurate delivery amounts at variable speeds, operates with minimal lateral movement, accommodates any configuration of composite carpules, allows for directional composite feed and it can be braced off the patient's jaw.

The prior art devices are cumbersome and bulky which is of major concern. The visibility into the patient's mouth is severely limited as is and any additional equipment just worsens the situation. The dentist works through a set of magnifying glasses and must readjust these every time he has to relocate the device in the patient's mouth or when he loses perspective of the device with respect to the cavity.

Large devices do not lend themselves to bracing against the patient's jaw for composite delivery. Corded and manual pressure actuated devices lack stability and tend to move during delivery. The carpules have to be changed frequently as the contents are often blended for color and transparency effects. This necessitates transfer of the device from the dentist to the dental assistant, across the intervening patient. Complicating this, the composite dries quickly and is light sensitive, so it must be applied correctly and quickly the first time.

Figure 1:
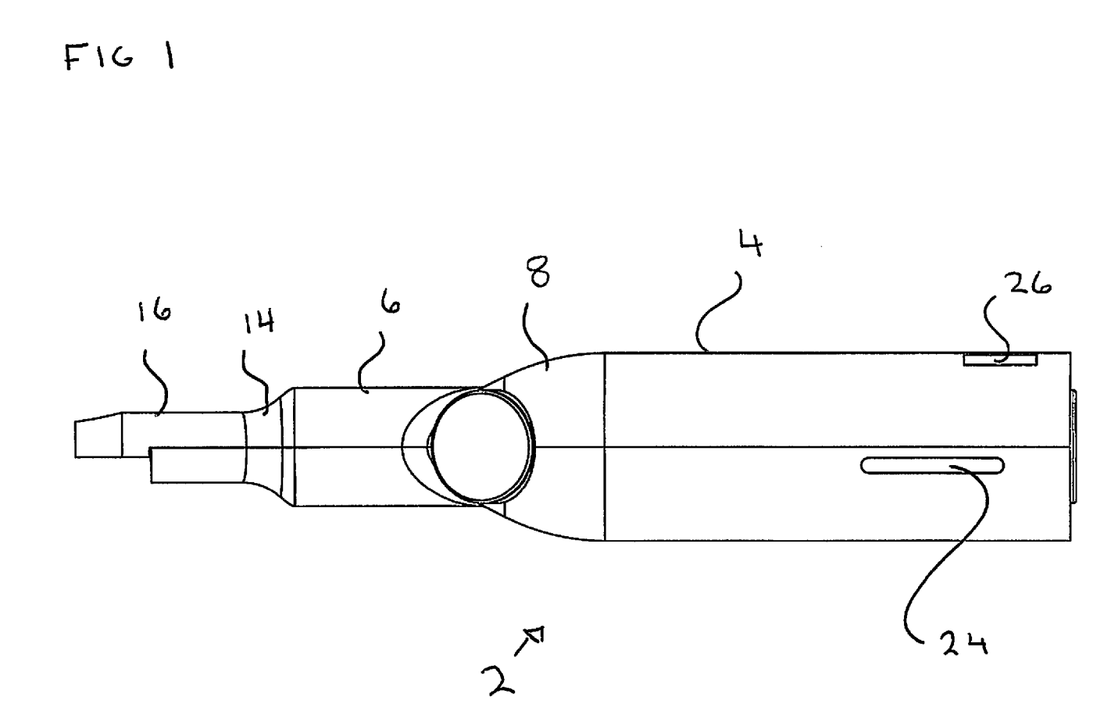
FIG. 1 is a top view of the composite extraction pen/ram retracted.
Figure 2:
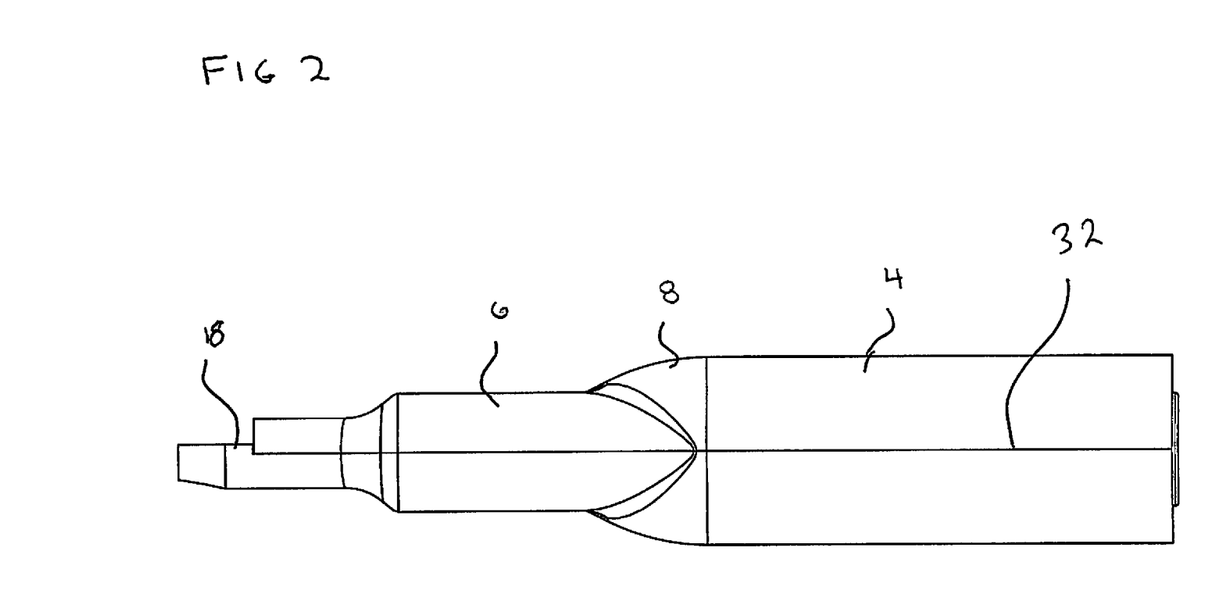
FIG. 2 is a bottom view of the composite extraction pen/ram retracted.
Figure 3:
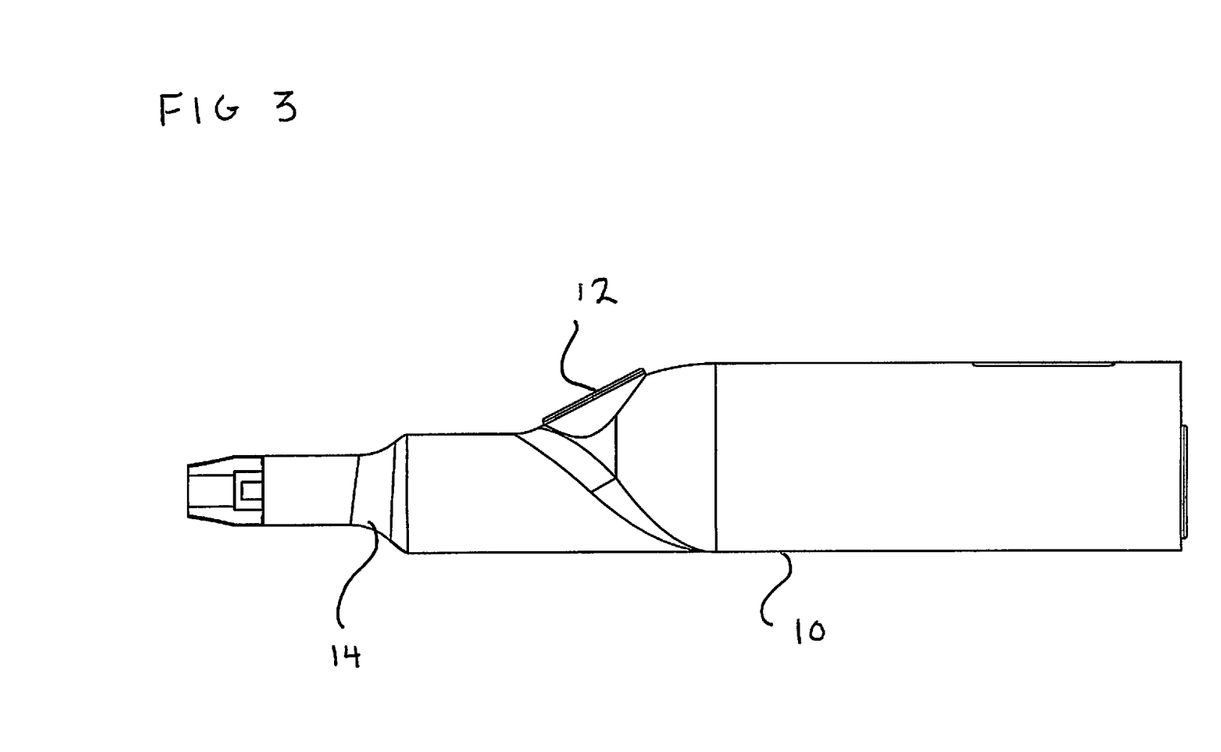
FIG. 3 is a right side view of the composite extraction pen/ram retracted.
Figure 4:
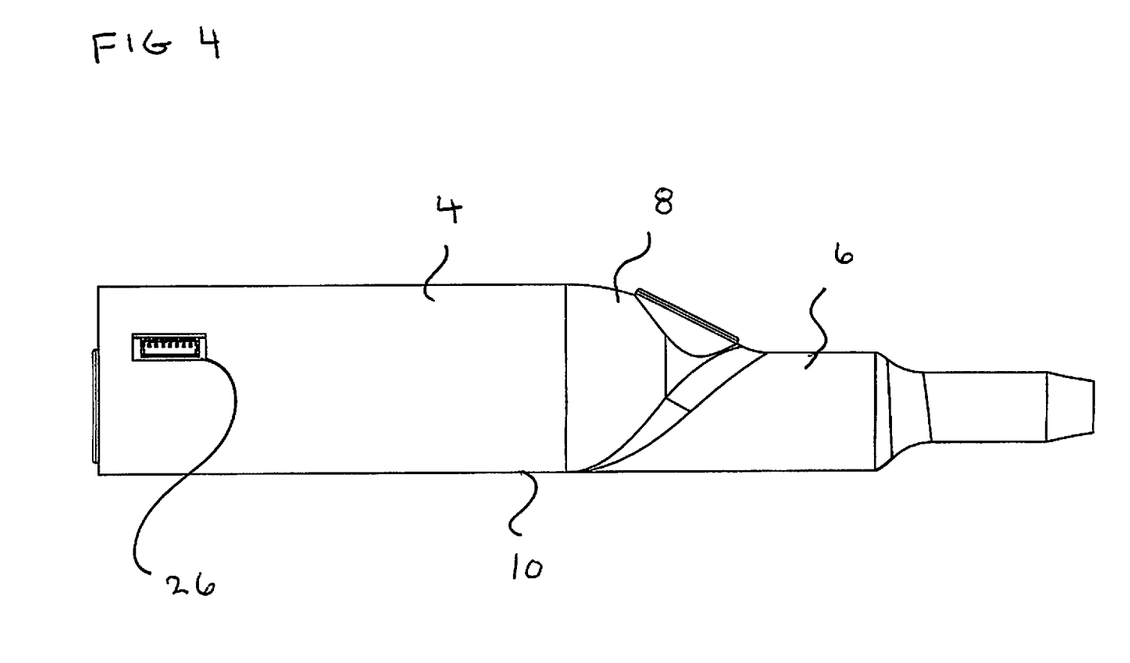
FIG. 4 is a left side view of the composite extraction pen/ram retracted.
Figure 5:
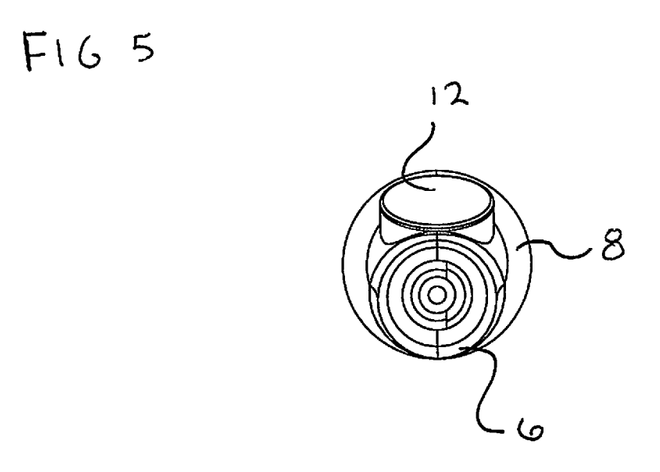
FIG. 5 is a front end view of the composite extraction pen.
Figure 6:
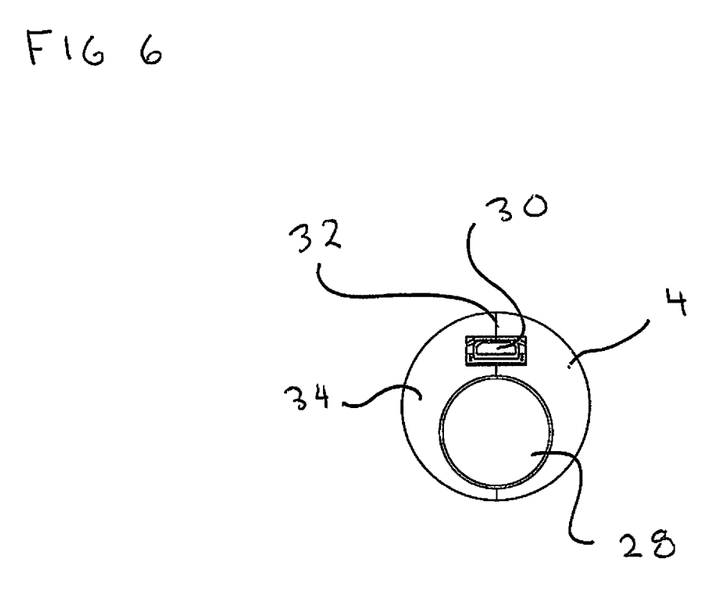
FIG. 6 is a back end view of the composite extraction pen.

Looking at FIGS. 1-6 the bare dental composite extraction pen 2 with its extraction ram in a retracted configuration, can be seen from all angles. The pen 2 has a ergonomically comfortable, generally cylindrical, polymer housing. The housing has a cylindrical, proximal grip section 4 having a diameter larger than the diameter of the cylindrical, distal feed section 6. Between these sections is a transitional region 8 that is tapered from the top and side faces of the grip section 4 toward the feed section 6. The two sections share a common horizontal, bottom axis 10 (FIGS. 3 and 4). The pen 2 is made in approximate half sections for assembly and disassembly. The mating seam 32 can be seen in FIGS. 32 and 6.

The feed section 6 also has a dual concentric cylinder design, (where they share a common axis) however, the transitional section 14 tapers uniformly 360 degrees between the cylinders such that their common axis lies along the cross sectional midpoint of the feed section 6. Engaged to the proximal end of the feed section 6 is the interchangeable carpule tip 16. This carpule tip 16 is a hollow cylinder that has a section beginning at its proximal end, that has half (180 degrees) of its sidewall 18 partially removed along its length. (FIGS. 1 and 2). It is sized for specific carpules 20. (FIG. 9) The inner bore of the carpule tip 16 is stepped (FIG. 12) such that it can retain a carpule in a linear aligned fashion, locating it based on the carpule's rear flange 22. (FIG. 9)

Located centrally along the transition region 8 is the tactile feed button 12 (FIGS. 3 and 5) that initiates the ram actuation. Along the right side of the pen 2 toward the rear of the grip section 4 is the visual ram speed indicator 24. (FIG. 1) It is ergonomically located so as to visible at all times of operation. In the preferred embodiment this is a linear array of LED lights that increase with the ram speed. On the left side of the pen 2 at the rear of the grip section 4 is the data port 26. (FIG. 4) At the proximal end of the grip section 4 is the rear plate 34. (FIG. 6) From the rear plate 34 extends the ram speed and retraction button 28. The charging port 30 is also located on the rear plate 34.

Figure 7:
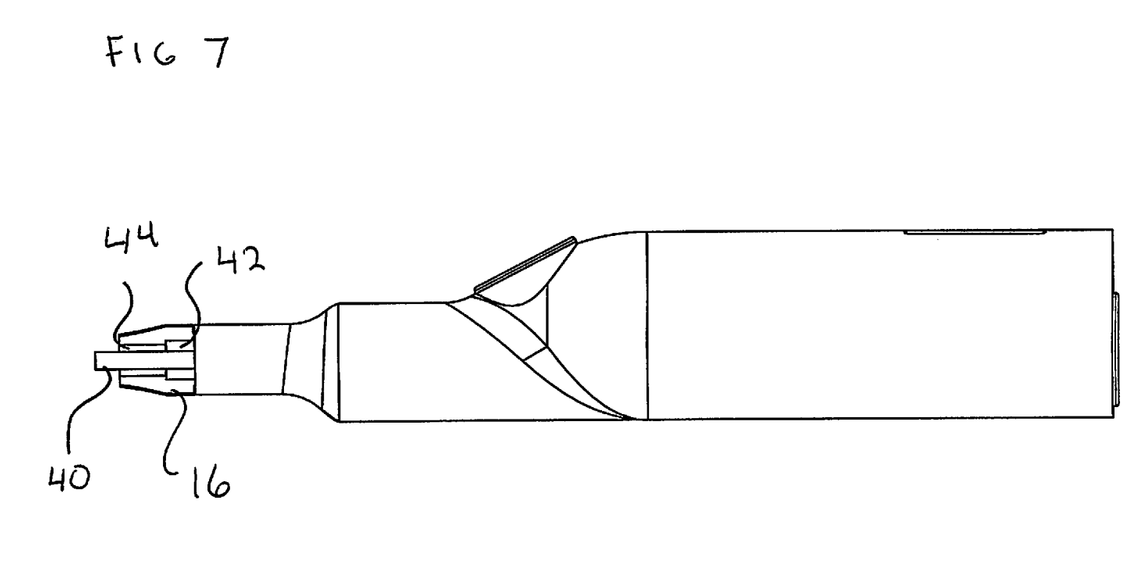
FIG. 7 is a right side view of the composite extraction pen/ram extended.
Figure 8:
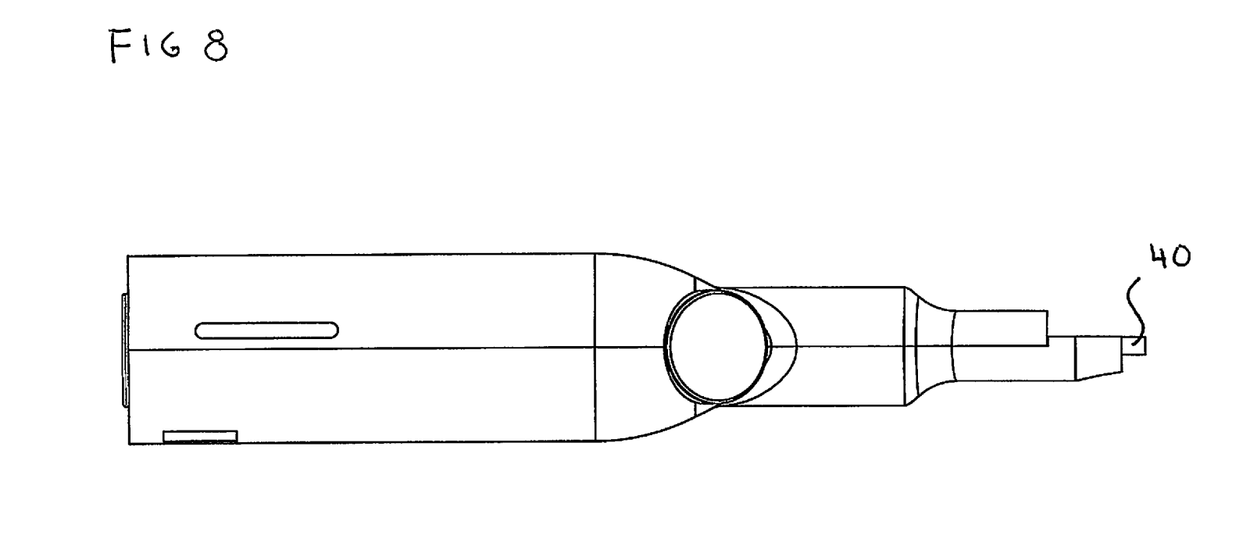
FIG. 8 is a top view of the composite extraction pen/ram extended.

FIGS. 7 and 8 illustrate the ram 40 in its fully extended state without a carpule 20 in the carpule tip 16. The stepped configuration of the carpule tip 16 showing the inner bore 42 and outer bore diameters 44 can best be seen in FIG. 8.

Figure 9:
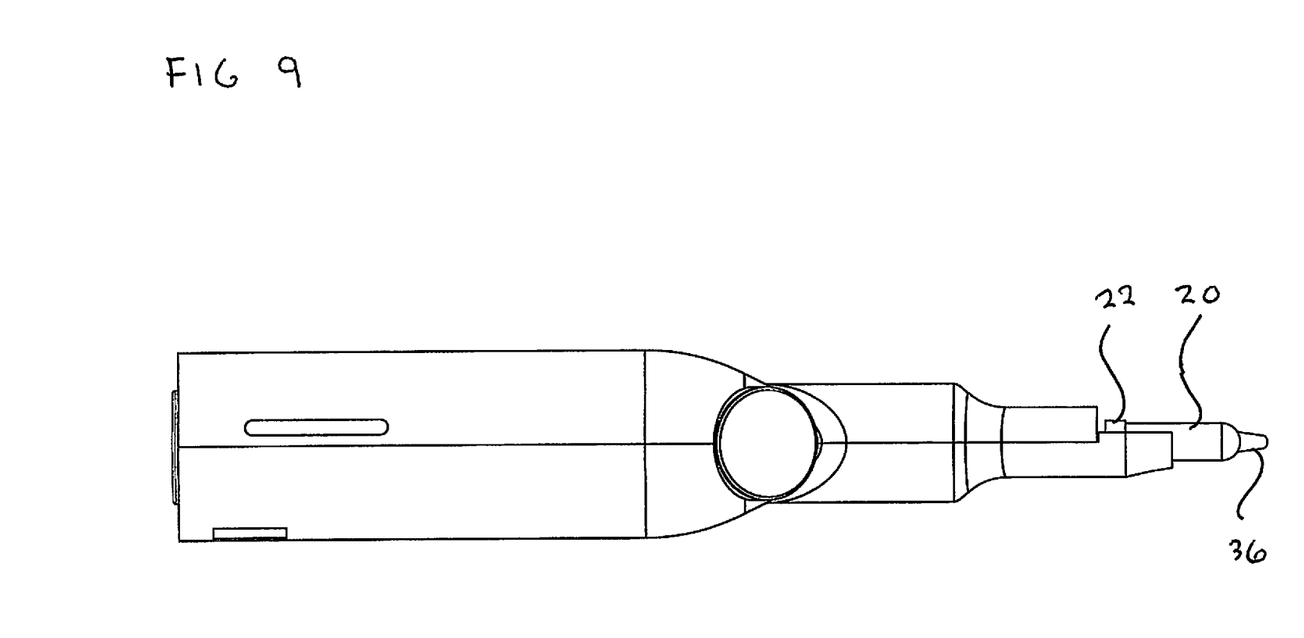
FIG. 9 is a top view of the composite extraction pen with a carpule.
Figure 10:
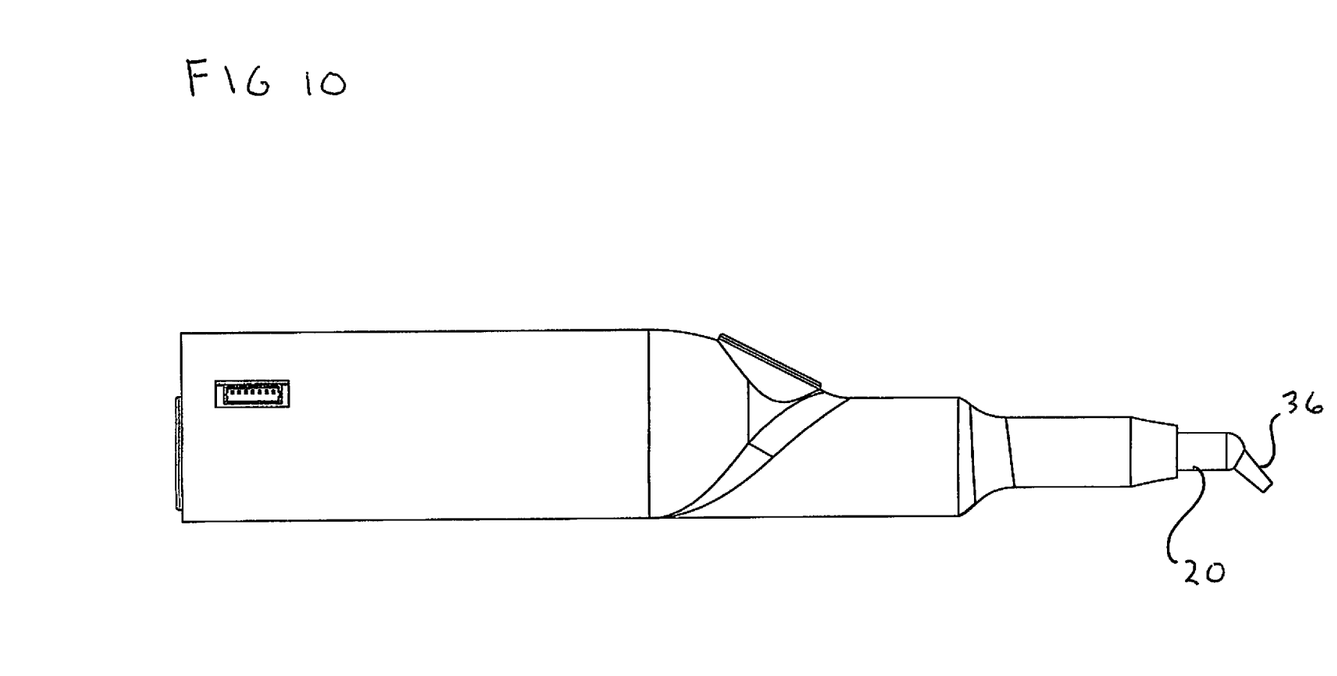
FIG. 10 is a side view of the composite extraction pen with a carpule.
Figure 11:
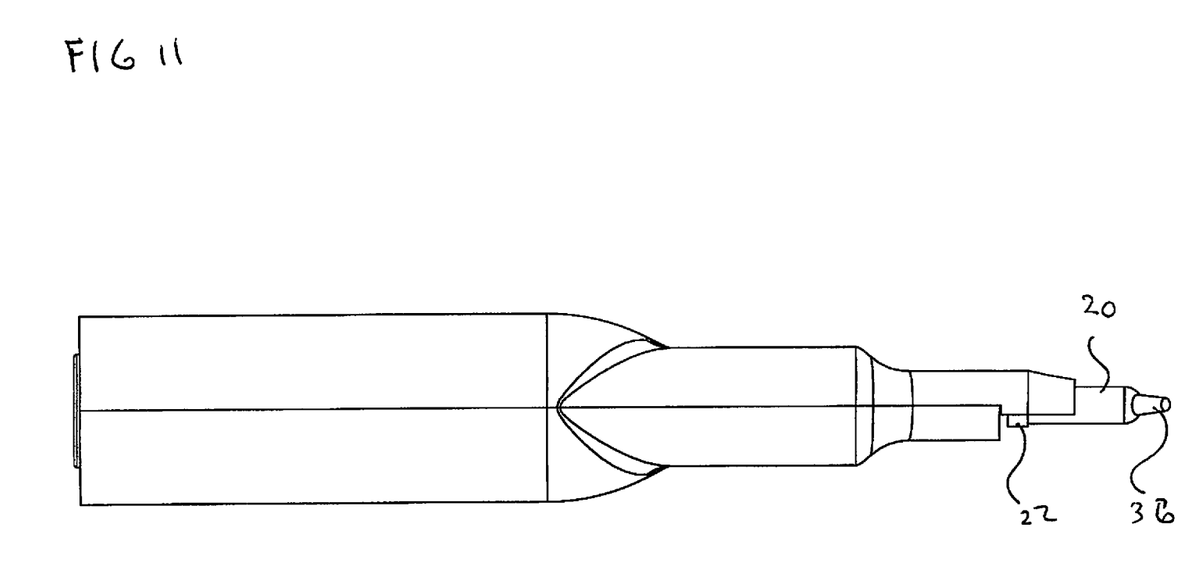
FIG. 11 is a bottom view of the composite extraction pen with a carpule.

FIGS. 9, 10 and 11 illustrate the pen 2 with the carpule 20 installed into the carpule tip 16. Here one can see a conventional, commercially available dental filling composite carpule 20. It is a hollow polymer shell with a linear bore, openable at both ends and bent at an acute angle along its length towards the distal tip 36. The proximal end has a raised peripheral rear flange 22 about its largest diameter opening 8. The ram is sized for sliding engagement within this linear bore. The carpule is aligned within the carpule tip 16 such that its longitudinal axis is common with the longitudinal axis of the ram. The distal end 10 has a smaller diameter opening (not illustrated) and a frictionally engageable cap (not illustrated). Between the openings, within the bore is a volume of dental composite, sealed from the atmosphere and light at the distal end by the cap and at the proximal end, by a delivery cup (not illustrated) that is frictionally inserted within the bore of the carpule, abutting the composite. When the cap is removed and a pressure is exerted onto the delivery cup, the delivery cup slides within the bore and composite is forced out of the smaller diameter opening at the distal end. It is this distal end opening that directs the composite into the patient's cavity. The carpule 20 may be rotated 360 degrees within the carpule tip 16 since the carpule tip has an open distal end that the carpule extends from allowing the distal end opening to swing about an arc with respect to the linear axis of the carpule tip. This allows the dentist great flexibility in the location of the pen 2 while he is filling cavities. The pen need not be inverted to fill upper teeth. The composite material may any one of the commercially available, proprietary formulations. As such, the consistency and flowability varies. For this reason, a high torque linear motor mated to a high power battery is utilized.

Figure 12:
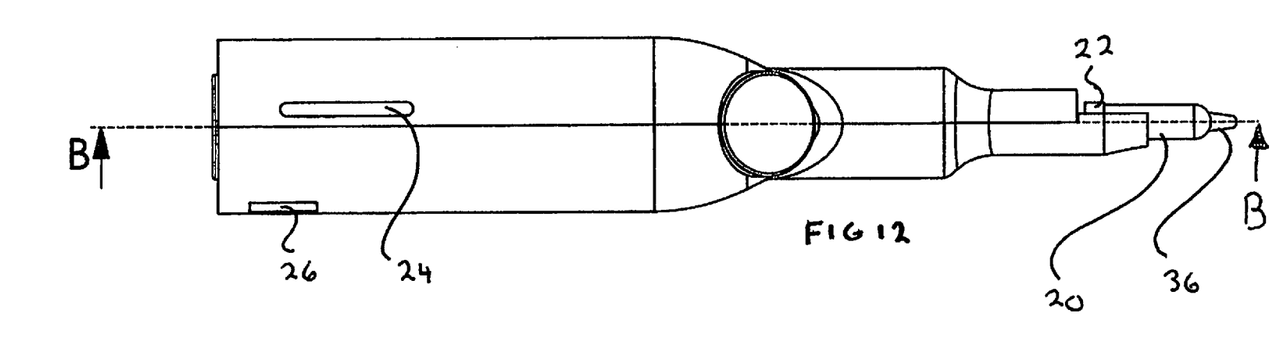
FIG. 12 is a top view of the composite extraction pen.
Figure 13:
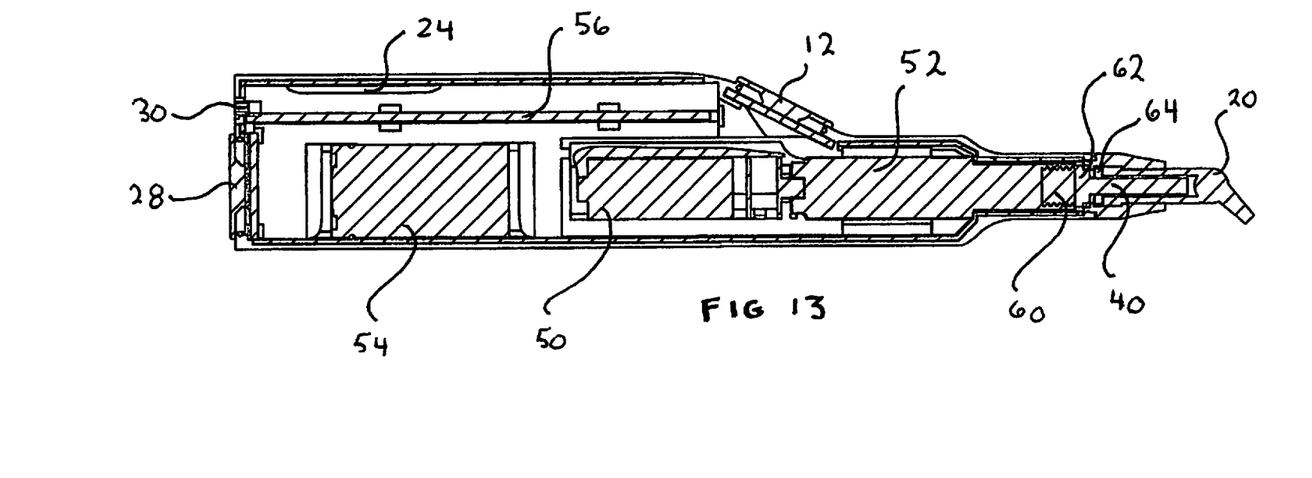
FIG. 13 is a side cross sectional view taken through section line BB of FIG. 12.

Looking at FIG. 13 which is a side cross sectional representation of the composite extraction pen 2 taken through line BB of FIG. 12, the internal components of the pen 2 can be seen. In this illustration a carpule 20 has been installed and the ram 40 has been extended so as to contact the cup in the end of the carpule 20 and advance it along the linear bore so as to force the composite out of the distal end of the carpule 20 and advance it along the linear axis of the carpule 40. For visual clarity any hard wiring has been eliminated from this view.

In the back of the grip section 4 is the rechargeable battery 54. In the preferred embodiment this is a 3.7 V LiMn 700 mAh high current battery with a18350 form factor (or larger power battery) that is affixed by soldering in place. This is operably connected to power all functions of the pen 2. Above the battery 54 is the microprocessor 56. Ahead of the distal end of the battery 54 is an electric, variable speed, high torque motor 50 which is connected to the linear actuator 52. (Together these form the linear actuator assembly.) In the preferred embodiment the peak motor draw is nominally 2.5 A. At the distal end of the linear actuator 52 there is an aluminum ram 40 which threads into the linear actuator 52. The linear actuator 52 is aligned within the pen 2 so as to have the centerline of so as to ram 20 common with the centerline of the carpule tip 16.

The ram 40 has a threaded section 60, a base 62, and in the preferred embodiment, a length of approximately 22 mm of which 20 mm may be extended into a carpule 20. The preferred embodiment ram has an approximately 2 mm thick retainer 64 that accounts for the remainder of the 22 mm. The full length of ram's extension is just over 20 mm, to ensure that when it protrudes from the end of the linear actuator 52 it is capable of extending 20 mm from into the bore of the carpule 20 and that when fully retracted, the ram is less than 0 mm into the carpule 20. (In this way the carpule can be completely evacuated by the ram 20.)

The ram speed and retraction button 28, the ram feed button 12, the battery 54, battery power indication lights, the motor 50, the visual ram speed indicator circuit, the battery charging port 30 and the data port 26 are all operably connected to the microprocessor 56 for the directional and speed control of the ram 40, the visual ram speed LED illumination, and the battery power LED illumination as would be known by a person of ordinary skill in the art. The speed and ram retraction switch directs the microprocessor to adjust the ram extension speed of the linear actuator, and the microprocessor processes and sends the LED illumination signals to the ram speed indicator circuit. (In the prototype pens, the microprocessor also has a data logging circuit with a real time clock that captures number of uses per set cycle, the battery state, the ram speed and length of ram extension per use. This data is stored in the transient memory of the microprocessor and is accessible via the data port 26. The microprocessor's ram speed circuit uses an accelerometer for the ram speed feedback)

The composite extraction pen 2 is housed within a slender, ergonomic linear member similar in shape to a pen. It's microprocessor 56 variably controls the speed of the motor 54 (and thus the speed of the ram extension) via actuation of the ram speed and retraction button 28. In the preferred embodiment, the peak speed of ram 20 (motor under load at maximum drive) is 2.43 mm/sec and the slowest speed of the ram 20 (motor under load at minimum drive) is 0.39 mm/sec. In the preferred embodiment, the microprocessor is a Cypress PSoC4 BLE, with a 32-bit ARM Cortex-M0 core capable of running up to 48 MHz. The SoC portion (configurable hardware similar to FPGA) handles some motor PWM timing requirements.

This button also controls the direction of the motor's rotation (and thus whether the ram extends or retracts). This button is located at the proximal end of the pen 2 specifically so that there could be no inadvertent alterations to the composite extraction feed speed. (Carpules are expensive.) It is to be noted that the advancement (extension) of the ram 20 is accomplished as long as the feed button 12 is depressed, (continual tactile manipulation) thereby allowing the dentist to extract any quantity of composite desired and to accomplish this in as small increments as they want. On the other hand the reversal (retraction) of the ram 20 is done at the highest rate of speed and in one continual motion by a single actuation of the ram speed and direction button.

The microprocessor 56 illuminates a series of LEDs in the visual ram speed indicator 24 that increase with increasing speed. The microprocessor also dictates the color of an imbedded power indication LED in the in the button 28. The length of the extension of the ram 20 is controlled by the length of time that the feed button 12 is depressed. The amount of ram extension (forward) travel is limited manually such that it will dispense the complete volume of the composite material through the smaller diameter opening of the carpule 20. The amount of travel required to empty a conventional carpule is 15-20 mm.

In the event of a weakened battery, a DC electric charging cable may be connected to the pen 2 via the charging port and the dentist may continue to use the device, albeit in a corded function. In alternate embodiments an inductive charging circuit may be utilized.

The carpule tip 16 has a cutaway portion along its length. This cutout allows the removal/insertion of a carpule and it also allows the carpule 20 to be rotated to different angles for disbursement as the dentist prefers. The adaptor is available in various different sizes to accommodate different manufacturer's carpules 20.

In operation, the dentist presses either button once (ram speed and retraction button 28 or the ram feed button 12) to electrically awake the pen 2 as the device's software on the microprocessor shuts down the pen 2 after a preset number of seconds of inactivity. (In alternate embodiments, the microprocessor's accelerometer may be used to power up and shut down the pen.) The ram speed and retraction button 28 is depressed for a preset number of seconds (Preferably 3 seconds) which will retract the ram 12 at full speed until it is fully retracted. The old carpule 20 can be removed and a new one inserted into the carpule tip 16 via the cutout. (At this time if a different manufacturer's carpule is to be used, an interchangeable carpule tip 16 may be substituted, and the carpule 20 may be oriented to the desired fill angle.) The carpule 20 is located such that its raised peripheral rear flange 22 abuts the inner stepped bore of the carpule tip 16. The ram feed button 12 is depressed momentarily so as to advance the ram 20 into the proximal end of the carpule up to the cup. The speed and retraction button is pressed numerous times to incrementally increase the speed of the ram and illuminate more LEDS in the visual ram speed indictor 24. (It is important that the speed of the ram corresponds to the flow speed of that specific composite.) Pressing the ram feed button 12 drives the motor 50 at the desired speed which causes the mechanically coupled linear actuator 52 to drive the ram 20 forward. The ram, in contact with the cup, forces composite to extrude from the distal end of the carpule. When a new carpule is required, the process is repeated. The power LED light will be red when the battery is critically low, yellow when the battery is low and green as long as there is 50% of the battery's capacity remaining.

It is important to note that many of the composites are extremely stiff (little flowability) and require heating if they are to be extracted via a manual device. Otherwise the force required to extract the composite makes the dentist's hand move to much for accurate application into a cavity (force tremor). However with this pen 2, utilizing a high torque motor eliminates both the need to heat the composite and the force tremor.

While certain features and aspects have been described with respect to exemplary embodiments, one skilled in the art will recognize that numerous modifications are possible. Similarly, while certain functionality is ascribed to certain system components, unless the context dictates otherwise, this functionality can be distributed among various other system components in accordance with the several embodiments.

System components described according to a particular structural architecture may be organized in alternative structural architectures. Hence, while various embodiments are described with—or without—certain features for ease of description and to illustrate exemplary aspects of those embodiments, the various components and/or features described herein with respect to a particular embodiment can be substituted, added, and/or subtracted from among other described embodiments, unless the context dictates otherwise. Consequently, although several exemplary embodiments are described above, it will be appreciated that the invention is intended to cover all modifications and equivalents within the scope of the following claims.

What is claimed is:

1. A dental composite extraction pen comprising:
    a housing;
    a carpule tip conformed for the retention therein of a carpule of flowable, extractable material,
    a tactile feed switch affixed to said housing;
    a power source therein said housing;
    a variable speed linear actuator assembly with an extendable ram, said linear actuator assembly therein said housing and operatively connected to said power source for the extension of said ram by actuation of said tactile switch;
    a microprocessor in said housing;
    a ram speed indicator circuit operatively connected to said microprocessor having a series of speed sensor LEDs, said LEDs mounted on said housing;
    a ram speed and retraction switch operationally mounted on said housing;
    wherein said speed and ram retraction switch directs said microprocessor to adjust an extension speed of said ram, and
    wherein said microprocessor processes and sends an LED illumination signal to the ram speed indicator circuit.

2. The composite extraction pen of claim 1 further comprising a battery power indication light.

3. The composite extraction pen of claim 1 wherein said ram may be extended or retracted, said extension controlled by continued tactile manipulation of said feed switch and said ram retraction is controlled by actuation of said ram speed and retraction switch.

4. The composite extraction pen of claim 1 further comprising;
    a microprocessor in said housing;
    a ram speed indicator circuit operatively connected to said microprocessor having a series of speed sensor LEDs, said LEDs mounted on said housing;
    a ram speed and retraction switch operationally mounted on said housing;
    wherein said speed and ram retraction switch directs said microprocessor to incrementally adjust an extension speed of said ram and a direction of said ram, and
    wherein said microprocessor processes and sends an LED illumination signal to the ram speed indicator circuit.

5. The composite extraction pen of claim 4 further comprising a battery power indication light.

6. The composite extraction pen of claim 4 wherein said ram may be extended or retracted, said extension controlled by continued tactile manipulation of said feed switch and said ram retraction is controlled by actuation of said ram speed and retraction switch.

7. The composite extraction pen of claim 1 wherein said carpule tip is interchangeable and has a partially removed cylindrical sidewall with an internal stepped bore configuration that matingly conforms to said carpule.

* * * * *